(12) United States Patent
Liang et al.

(10) Patent No.: US 8,199,478 B2
(45) Date of Patent: Jun. 12, 2012

(54) ELECTRONIC DEVICE AND SLIDING ASSEMBLY THEREOF

(75) Inventors: Yuan-Chen Liang, Taipei (TW); Cheng-Wang Lin, Taipei County (TW); Jui-Lan Yu, Taipei County (TW); Chia-Hui Wu, Chiai County (TW); Hung-Ching Chen, Taipei County (TW)

(73) Assignee: Quanta Computer Inc., Kuei Shan Hsiang, Tao Yuan Shien (TW)

( * ) Notice: Subject to any disclaimer, the term of this patent is extended or adjusted under 35 U.S.C. 154(b) by 332 days.

(21) Appl. No.: 12/551,622

(22) Filed: Sep. 1, 2009

(65) Prior Publication Data
US 2010/0309612 A1  Dec. 9, 2010

(30) Foreign Application Priority Data
Jun. 4, 2009 (TW) .............................. 98209772 U

(51) Int. Cl.
*G06F 1/16* (2006.01)
(52) U.S. Cl. ............ 361/679.3; 361/679.55; 361/679.56; 312/223.1; 312/223.2; 455/575.1; 455/575.4
(58) Field of Classification Search ................ 361/679.3
See application file for complete search history.

(56) References Cited

U.S. PATENT DOCUMENTS

| 7,369,884 | B2 * | 5/2008 | Park et al. .................. 455/575.4 |
| 7,403,612 | B2 * | 7/2008 | Nishihara ................ 379/433.12 |
| 7,853,300 | B2 * | 12/2010 | Seidler ........................ 455/575.4 |
| 7,925,310 | B2 * | 4/2011 | Chiu .......................... 455/575.1 |
| 2005/0164751 | A1 * | 7/2005 | Nishihara .................. 455/575.1 |
| 2009/0082074 | A1 * | 3/2009 | Chen .......................... 455/575.4 |
| 2010/0033910 | A1 * | 2/2010 | Wang et al. .............. 361/679.01 |
| 2010/0226080 | A1 * | 9/2010 | Tsuchida et al. .......... 361/679.01 |

* cited by examiner

*Primary Examiner* — Anthony Q Edwards
(74) *Attorney, Agent, or Firm* — Thomas|Kayden

(57) ABSTRACT

An electronic device includes an upper cover and a main body. A sliding assembly is disposed between the upper cover and the main body and includes a sliding portion, a spring, and a track with a first positioning portion disposed at the center of a side of the track and two second positionings portion disposed on two ends of the side of the track. The spring including an engaging portion and two ends, and the sliding portion are fixed on the cover. The engaging portion and the ends form an included angle. The sliding portion is movably connected to the track and slides thereon. When the sliding portion slides on the track, the engaging portion is engaged with one of the first positioning portion and the second positioning portions.

17 Claims, 6 Drawing Sheets

ELECTRONIC DEVICE AND SLIDING ASSEMBLY THEREOF

CROSS REFERENCE TO RELATED APPLICATIONS

This Application claims priority of Taiwan Patent Application No. 098209772, filed on Jun. 4, 2009, the entirety of which is incorporated by reference herein.

BACKGROUND OF THE INVENTION

1. Field of the Invention

The invention relates to an electronic device and a sliding assembly thereof.

2. Description of the Related Art

FIG. 1 is a schematic view of a conventional slidable electronic device. FIG. 2 is an exploded view of a slidable structure of a conventional slidable electronic device. Referring to FIG. 1, the conventional electronic device 10 includes a main body 11 and an upper cover 12. A key portion 111 is disposed on the main body 11. The upper cover 12 slides on the main body 11. Referring to FIG. 2, a track 122 is disposed on a bottom surface 121 of the upper surface 12, and a track 113 is disposed on a top surface 112. A slidable block 13, a rotatable base 14, a spring 15, a linking bar 16 and an axle 17 are connected with each other and disposed between the tracks 122 and 113. The slidable block 13 is coupled with and corresponds to the track 122. The slidable block 13 moves toward and backward along the track 113. The rotatable base 14 is connected to the slidable block 13. When the slidable block 13 moves, the rotatable base 14 moves along the track 122. The linking bar 16 rotates axially along the track 113, thus, the standing angle of the upper cover 12 is decided. One end of the main body passes through the axle 17 via the spring 15 and is connected to one end of the rotatable base 14. The axle 17 is used to fix the connection between the rotatable base 14, the track 113 and the spring 15. The spring 15 provides support for the upper cover 12.

In summary, the structure of the conventional electronic device 10 is complex and potential decrease in costs of the complex structure is limited.

BRIEF SUMMARY OF THE INVENTION

The invention provides a sliding assembly comprising a sliding portion, a spring, and a track. The spring comprises an engaging portion and two ends. The engaging portion and the two ends form an included angle. The track comprises a first positioning portion and two second positioning portions. The sliding portion is connected to the track and slides corresponding to the track. The first positioning portion is disposed on the central portion of the side of the track. The second positioning portions are respectively disposed on two ends of the side of the track. When the sliding portion slides corresponding to the track, the engaging portion engages with one of the first positioning portion and the second positioning portions.

Note that the included angle is an obtuse angle.

Note that the first positioning portion is a groove. The engaging portion is a protrusion. The first positioning portion is engaged with the engaging portion.

Note that the second positioning portions comprise a ditch and a wall.

Note that the sliding portion is a bar. The track comprises a long narrow groove. The sliding portion moves in the track.

The invention provides an electronic device comprising an upper cover and a main body. The upper cover comprises a sliding portion and a spring. The spring and the sliding portion are fixed to the upper cover, and the spring comprises an engaging portion and two ends. The engaging portion and the two ends form an included angle. The main body comprises a track. The track comprises a first positioning portion and two second positioning portions. The sliding portion is connected to the track and slides corresponding to the track. The first positioning portion is disposed on the central portion of the side of the track. The second positioning portions are respectively disposed on two ends of the side of the track. When the sliding portion slides corresponding to the track, the engaging portion engages with one of the first positioning portion and the second positioning portions.

Note that the main body further comprises an input device.

Note that the upper cover further comprises a screen.

BRIEF DESCRIPTION OF DRAWINGS

The invention can be more fully understood by reading the subsequent detailed description and examples with references made to the accompanying drawings, wherein.

The invention can be more fully understood by reading the subsequent detailed description and examples with references made to the accompanying drawings.

DETAILED DESCRIPTION OF THE INVENTION

Figure 1:
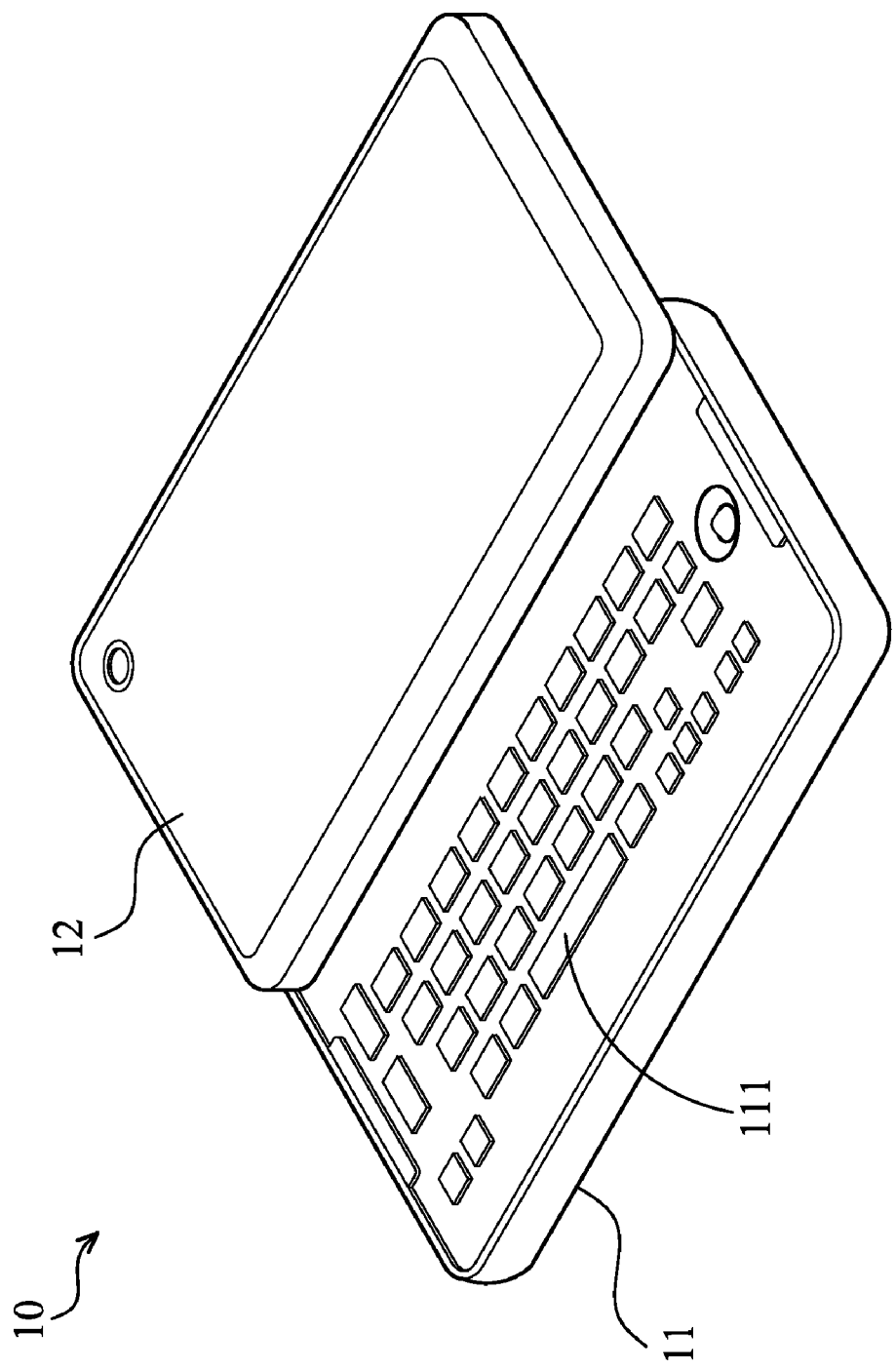
FIG. 1 is a schematic view of a conventional slidable electronic device.
Figure 2:
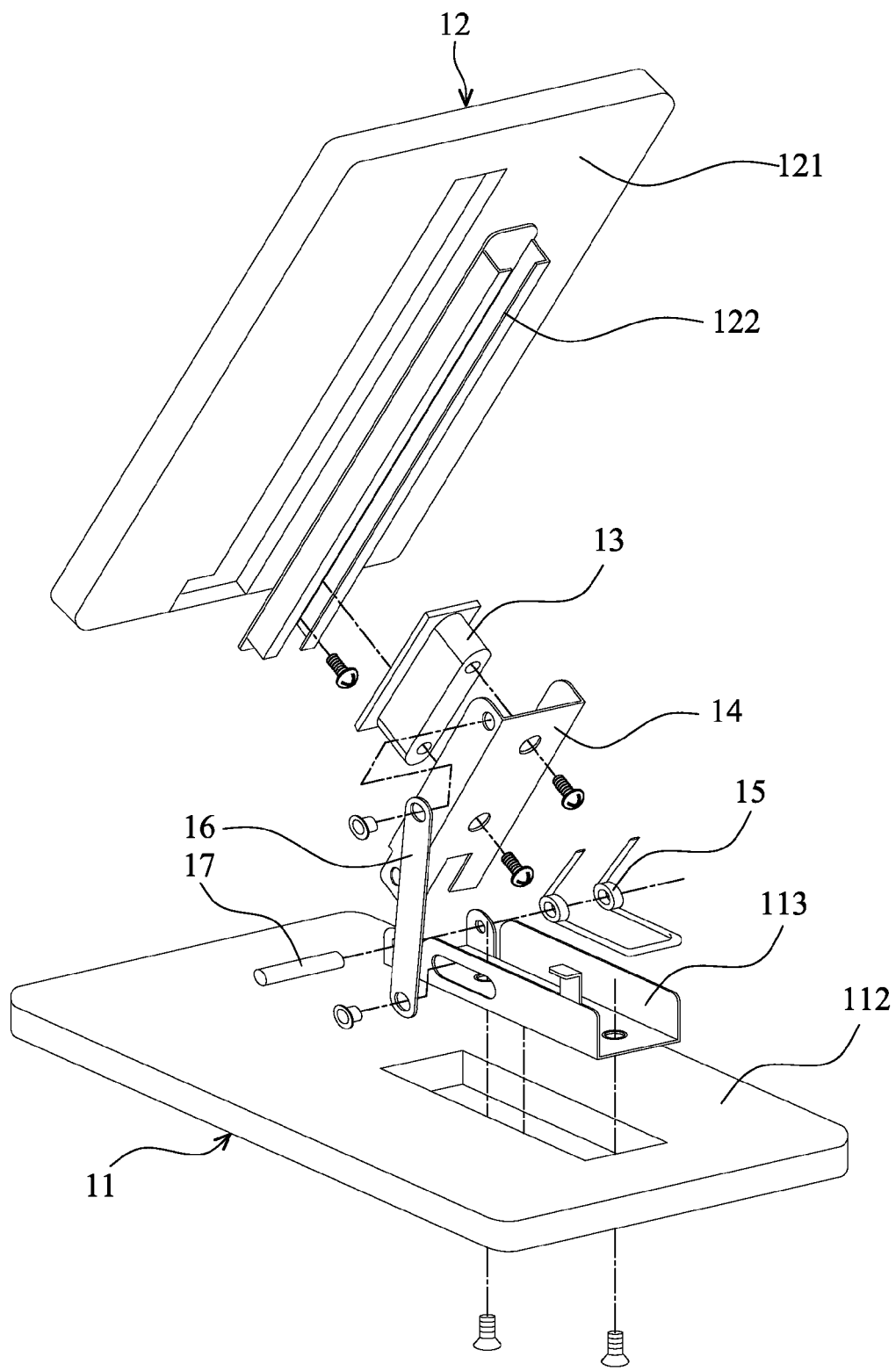
FIG. 2 is an exploded view of a slidable structure of a conventional slidable electronic device.
Figure 3:
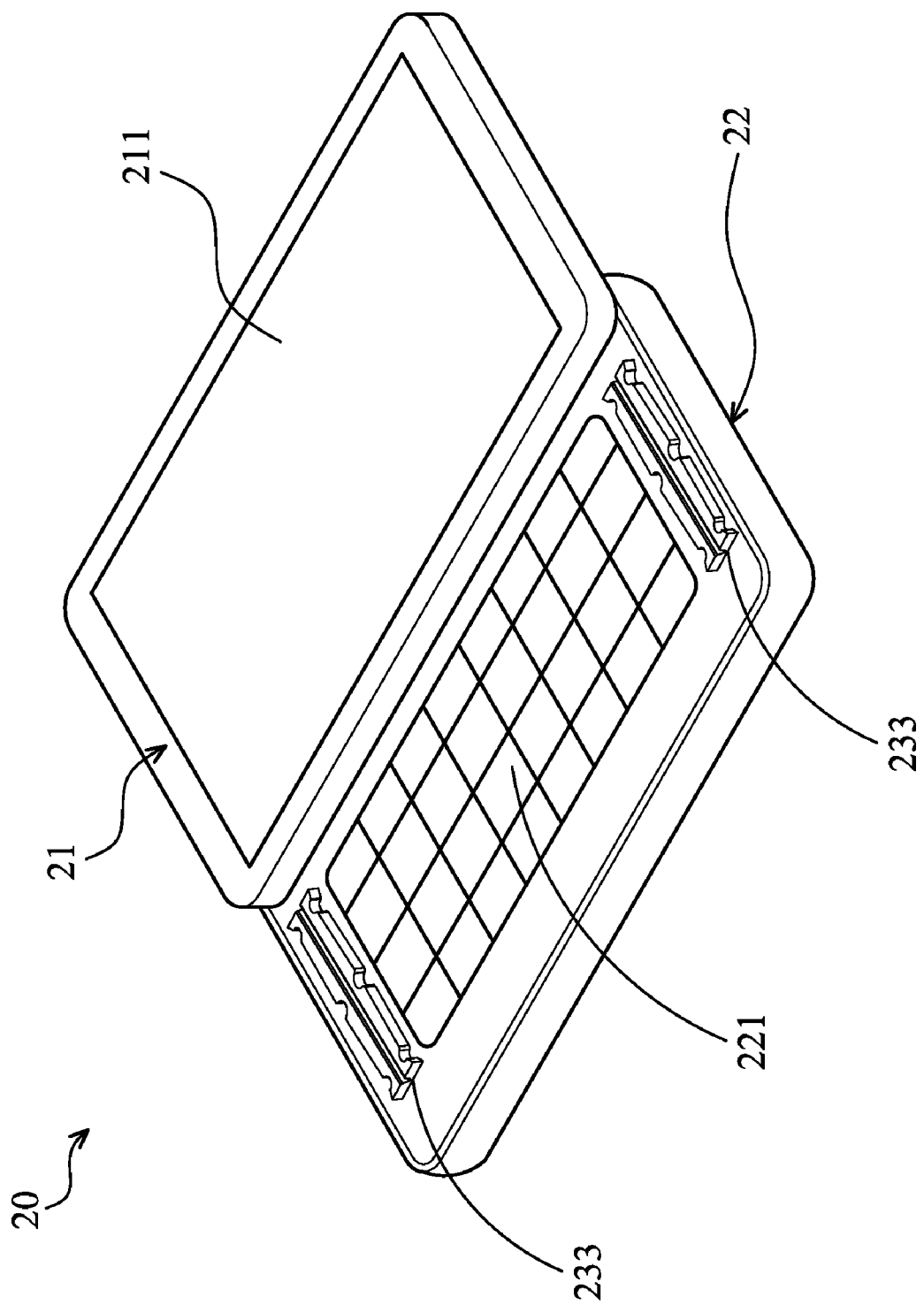
FIG. 3 is a schematic view showing an electronic device of the invention.
Figure 4:
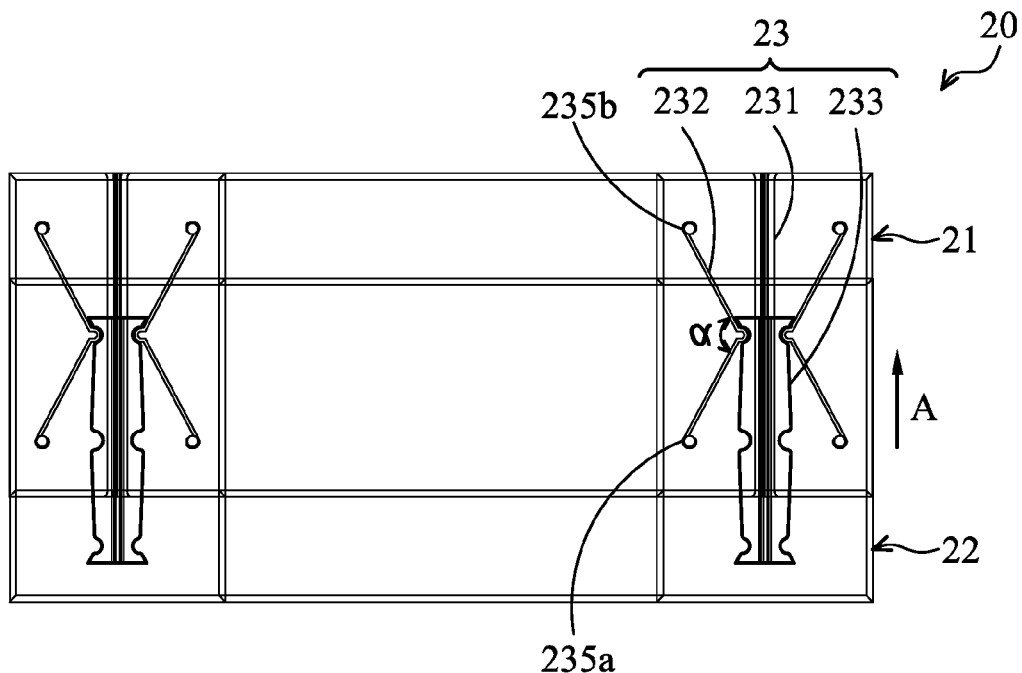
FIGS. 4 and 5 are schematic views showing a sliding upper cover of an electronic device.
Figure 5:
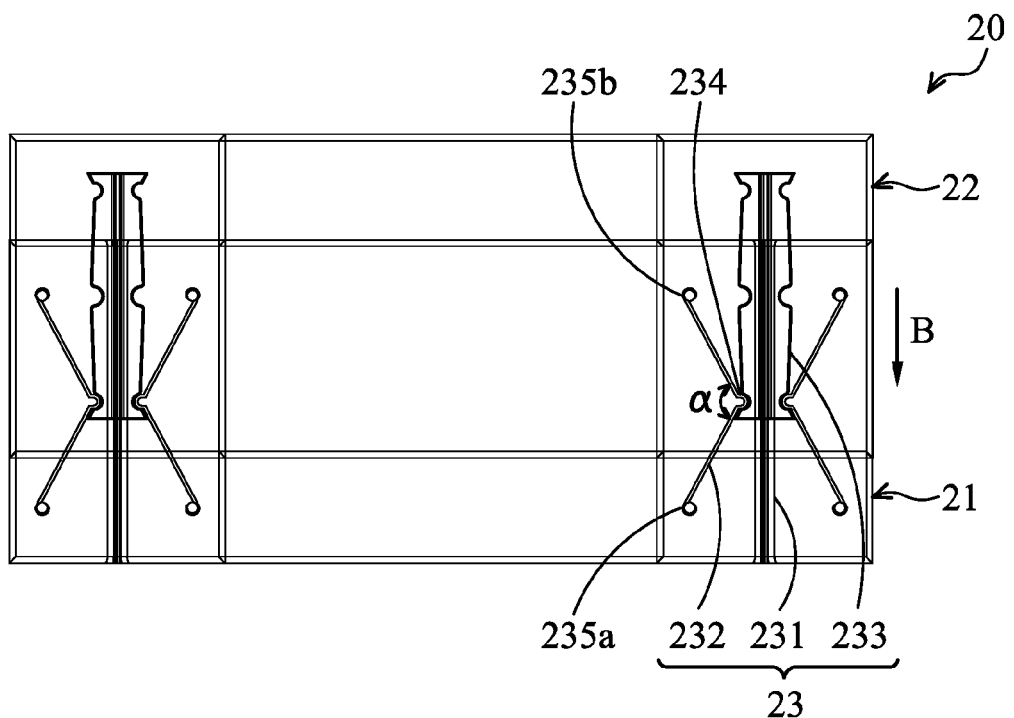
Figure 6:
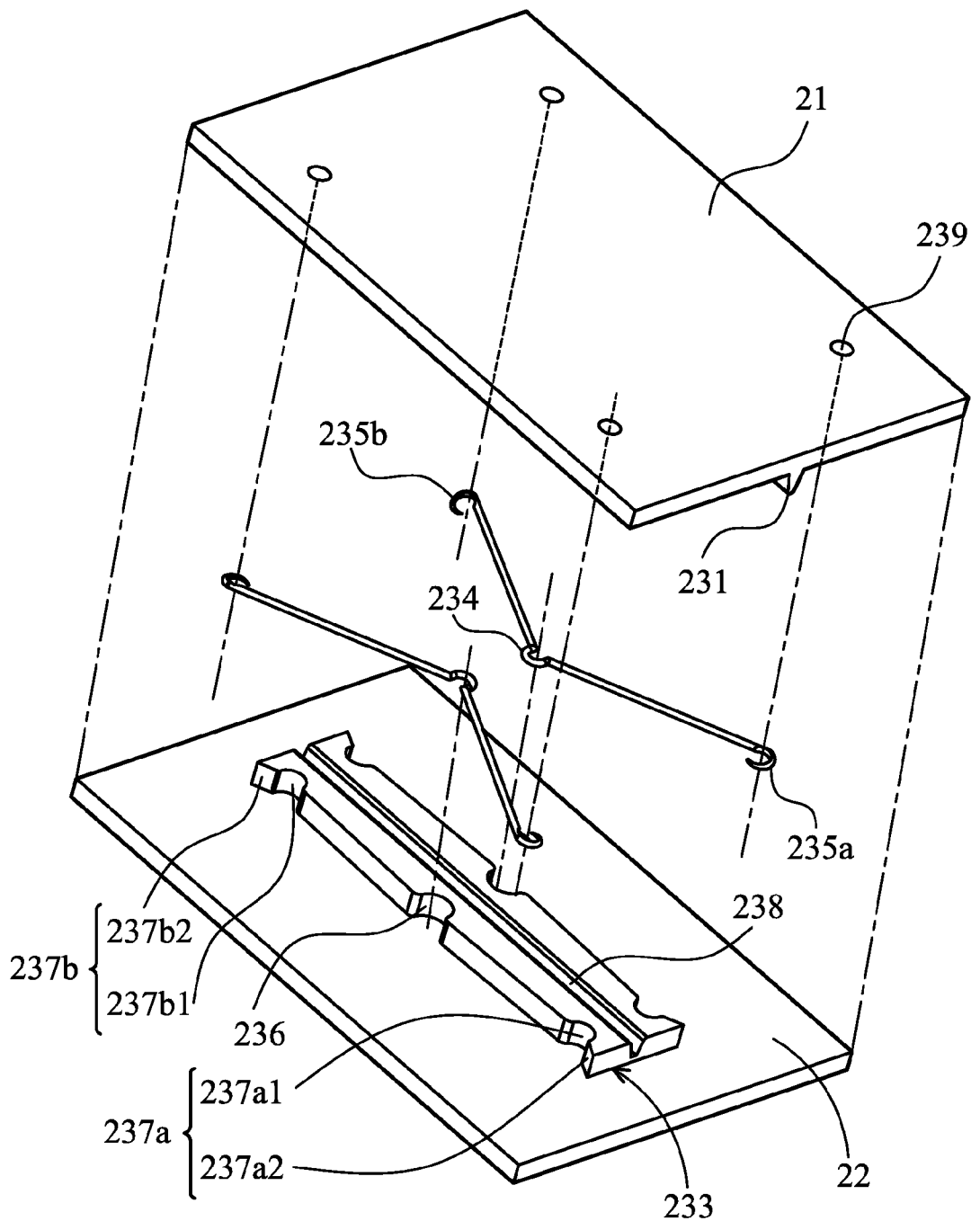
FIG. 6 is an exploded view showing a sliding assembly of an electronic device of the invention.

FIG. 3 is a schematic view showing an electronic device of the invention. FIGS. 4 and 5 are schematic views showing a sliding upper cover of an electronic device. FIG. 6 is an exploded view showing a sliding assembly of an electronic device of the invention. In the embodiment of an electronic device of the invention is, for example, a mobile internet device, MID, of a laptop or a notebook, or a cell phone etc., has an antenna module.

Referring to FIG. 3, an electronic device 20 of the invention comprises an upper cover 21 and a main body 22. The upper cover 21 comprises a screen 211. The main body 22 comprises an input device 221, for example, a key module or a touch panel module. When a user inputs commands to the electronic device 20 via the input device 221, the screen 21 shows the information image. The upper cover 21 slides corresponding to the main body 22 via a sliding assembly 23.

Referring to FIGS. 4-6, the sliding assembly 23 is disposed between the upper cover 21 and the main body 22. The sliding assembly 23 comprises a sliding portion 231, a pair of springs 232 and a track 233. The spring 232 and the sliding portion 231 are fixed to the upper cover 21. The springs 232 are symmetrically disposed on two sides of the track 233, and each spring 232 comprises an engaging portion 234 and two ends 235a and 235b. The engaging portion 234 and the ends 235a and 235b form an included angle α. In one embodiment, the sliding portion 231 and the spring 232 are disposed on the upper cover 21. The track 233 is disposed on the main body 22 and corresponds to the sliding portion 231 and the spring 232. In another embodiment, the sliding portion 231 and the spring 232 are disposed on the main body 22. The track 233 is disposed on the upper cover 21 and corresponds to the sliding portion 231 and the spring 232.

A first positioning portion 236 and two second positioning portions 237a and 237b are correspondingly disposed on right and left sides of the track 233. The sliding portion 231 is connected to the track 233 and slides corresponding to the track 233. In this embodiment, the first positioning portion 236 is disposed on the central portion of the side of the track 233. The second positioning portions 237a and 237b are respectively disposed on the two ends of the side of the track 233. When the sliding portion 231 slides corresponding to the track 233, the engaging portion 234 engages with one of the first positioning portion 236 and the second positioning portions 237a and 237b. Note that the amount of engaging portions is decided according to actual requirement. Also, as the amount of engaging portions increase, multi-staged fixation is achieved, wherein the adjustable area becomes greater for a user. In one embodiment, the additional engaging portions may be installed between the first positioning portion 236 and the second positioning portions 237a and 237b.

Note that the included angle α is an obtuse angle. The first positioning portion 236 is a groove. The engaging portion 234 is a protrusion. Thus, the first positioning portion 236 could be engaged with the engaging portion 234. The second positioning portions 237a and 237b respectively comprise ditches 237a1 and 237b1 and walls 237a2 and 237b2. When the engaging portion 234 moves to either of the two ends of the track 233, the ditches 237a1 or 237b1 and the walls 237a2 or 237b2 provides fixation and limits movement to avoid departure of the sliding portion 231 from the track 233. In this embodiment, the sliding portion 231 is a bar. The track 233 comprises a long narrow groove 238. The sliding portion 231 moves in the long narrow groove 238 of the track 233. The ends 235a and 235b of the spring 232 comprise two hooks. The upper cover 21 comprises a plurality of hooked portions 239 corresponding with the hooks to fix the spring 232 to the upper cover 21.

Referring to FIGS. 4 and 6, when the upper cover 21 moves on the main body 22 along the direction of arrow A, the sliding portion 231 moves along the track 233 and simultaneously the spring 232 departs from the first positioning portion 236. When the spring 232 moves on the side of the track 233, the included angle a becomes greater than the included angle a when the engaging portion 234 is disposed on the first positioning portion 236. At this time, the spring 232 is at a more pressed state, thus, the spring 232 provides a fastening force to slow down the sliding speed of the upper cover 21 corresponding to the main body 22. When the upper cover 21 moves to the position of FIG. 4, the engaging portion 234 is blocked by the ditch 237b1 and the wall 237b2 of the second positioning portion 237b, and the engaging portion 234 slides into the ditch 237b1 of the second positioning portion 237b. Furthermore, the wall 237b2 is provided so that the upper cover 21 does not continue moving along the direction as shown by arrow A, thus avoid sliding out from the main body 22.

Referring to FIGS. 5 and 6, when the upper cover 21 slides on the main body 22 along the direction shown in arrow B, the sliding portion 231 moves along the track 233 and simultaneously the spring 232 departs from the first positioning portion 236. When the spring 232 moves on the side of the track 233 the included angle α becomes greater than the included angle α when the engaging portion 234 is disposed on the first positioning portion 236. At this time, the spring 232 is at a more pressed state, thus, the spring 232 provides a fastening force to slow down the sliding speed of the upper cover 21 corresponding to the main body 22. When the upper cover 21 moves to the position of FIG. 5, the engaging portion 234 is blocked by the ditch 237a1 and the wall 237a2 of the second positioning portion 237a, and the engaging portion 234 slides into the ditch 237a1 of the second positioning portion 237a. Furthermore, the wall 237a2 is provided so that the upper cover 21 does not continue moving along the direction as shown by arrow B, thus avoid sliding out from the main body 22.

Figure 7:
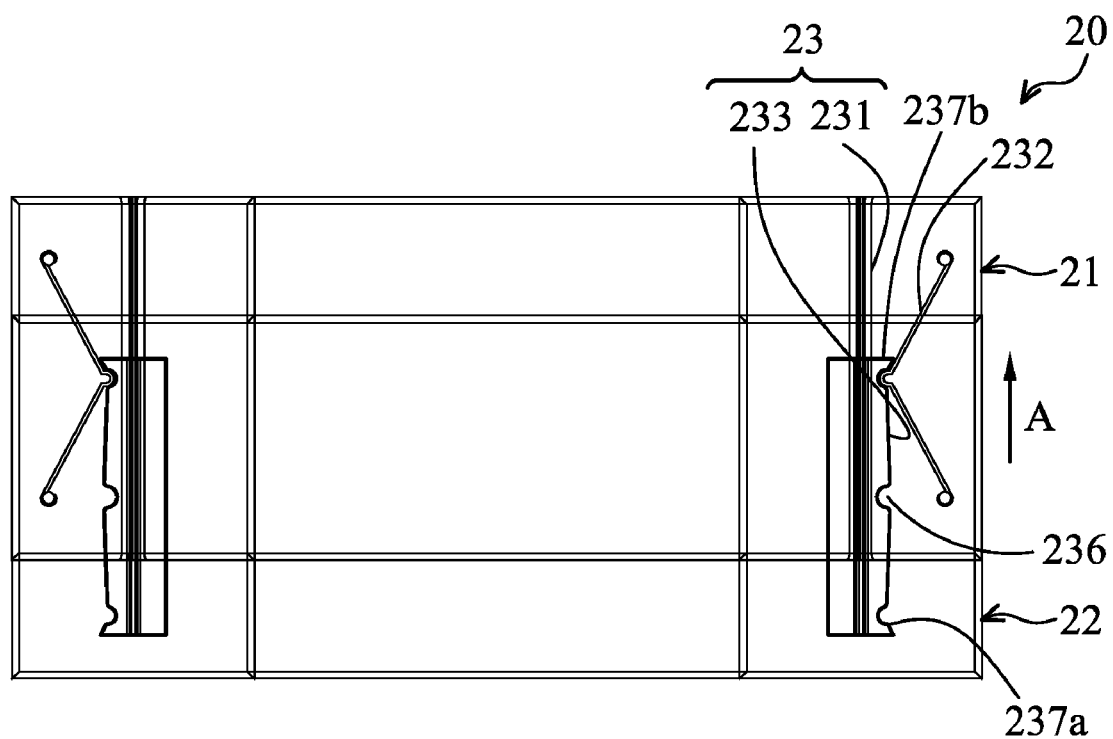
FIG. 7 is a schematic view showing a sliding assembly of an electronic device of another embodiment of the invention.

FIG. 7 is a schematic view showing a sliding assembly of an electronic device of another embodiment of the invention. All structures of FIG. 7 are approximately similar to those of FIG. 5. The difference is that the sliding assembly 23 comprises a single spring 232, and the first positioning portion 236 and the second positioning portions 237a and 237b are only disposed on the side where the single spring 232 is disposed. The side without the spring is a plane surface, as shown in FIG. 7. Actually, only one side of the track 233 needs to install the first positioning portion 236 and the second positioning portions 237a and 237b as long as the first positioning portion 236 and the second positioning portions 237a and 237b could be connected movably to the spring 232. However, the sliding assembly 23 of previous embodiment of FIG. 5 comprises a pair of springs for providing stable sliding efficiency.

In summary, the electronic device and the sliding assembly thereof of the invention allows the upper cover 21 of the electronic device 20 to move upward and downward corresponding to the main body 22 in a simplified manner, thus decreasing structural cost thereof and costs associated with assembly time.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A sliding assembly, comprising:
a sliding portion;
a spring, comprising an engaging portion and two ends, wherein the engaging portion and the two ends form an included angle; and
a track, comprising a first positioning portion and two second positioning portions, wherein the sliding portion slides corresponding to the track, the first positioning portion is disposed on a central portion of a side of the track, and the second positioning portions are respectively disposed on two ends of the side of the track;
wherein when the sliding portion slides corresponding to the track, the engaging portion engages with one of the first positioning portion and the second positioning portions,
wherein the first positioning portion is a notch and the engaging portion is a protrusion.

2. The sliding assembly as claimed in claim 1, wherein the included angle is an obtuse angle.

3. The sliding assembly as claimed in claim 1, wherein the second positioning portions comprise a ditch and a wall for engaging the engaging portion and for limiting the engaging portion against movement, respectively.

4. The sliding assembly as claimed in claim 1, wherein the sliding portion is a bar, the track comprises a long narrow groove, and the sliding portion moves in the track.

5. An electronic device, comprising:
   an upper cover, comprising a sliding portion and a spring, wherein the spring and the sliding portion are fixed to the upper cover, and the spring comprises an engaging portion and two ends, wherein the engaging portion and the ends form an included angle; and
   a main body, comprising a track, wherein the track comprises a first positioning portion and two second positioning portions, the sliding portion slides corresponding to the track, the first positioning portion is disposed on a central portion of a side of the track, and the second positioning portions are respectively disposed on two ends of the side of the track,
   wherein when the sliding portion slides corresponding to the track, the engaging portion engages with one of the first positioning portion and the second positioning portions, wherein the ends of the spring comprise two hooks, the upper cover comprises a plurality of hooked portions, and the hooks are connected to the hooked portions to fix the spring to the sliding portion.

6. The electronic device as claimed in claim 5, wherein the included angle is an obtuse angle.

7. The electronic device as claimed in claim 5, wherein the first positioning portion is a groove and the engaging portion is a protrusion.

8. The electronic device as claimed in claim 5, wherein the second positioning portions comprise a ditch and a wall for engaging the engaging portion and for limiting the engaging portion against movement, respectively.

9. The electronic device as claimed in claim 5, wherein the sliding portion is a bar, the track comprises a long narrow groove, and the sliding portion moves in the track.

10. The electronic device as claimed in claim 9, wherein the first positioning portion is a groove and the engaging portion is a protrusion.

11. The electronic device as claimed in claim 10, wherein the second positioning portions comprises a ditch and a wall for engaging the engaging portion and for limiting the engaging portion against movement respectively.

12. The electronic device as claimed in claim 11, wherein the ends of the spring respectively comprise a hook, the upper cover comprises a plurality of hooked portions, and the hooks are connected to the hooked portions to fix the spring to the upper cover.

13. The electronic device as claimed in claim 12, wherein the main body further comprises an input device.

14. The electronic device as claimed in claim 13, wherein the upper cover further comprises a screen.

15. An electronic device, comprising:
    an upper cover, comprising a first sliding portion, a second sliding portion, a first spring and a second spring, wherein the first sliding portion and the second sliding portion respectively are fixed to sides of the upper cover, the first spring is fixed to a side of the first sliding portion, the second spring is fixed to a side of the second sliding portion, the first spring and the second spring respectively comprise an engaging portion and two ends, and the engaging portions and the ends form an included angle; and
    a main body, comprising a first track and a second track corresponding to the first sliding portion and a second sliding portion, wherein the first track and the second track respectively comprise a first positioning portion and two second positioning portions, the first positioning portions are respectively disposed on central portions of sides of the first track and the second track, and the second positioning portions are disposed on two ends of the sides of the first track and the second track;
    wherein when the first sliding portion and the second sliding portion slide respectively corresponding to the first track and the second track, the engaging portions engage with one of the first positioning portions and the second positioning portions, wherein the ends of the first spring and the second spring respectively comprise a hook, the upper cover comprises a plurality of hooked portions, and the hooks are connected to the hooked portions to fix the first spring and the second spring to the upper cover.

16. The electronic device as claimed in claim 15, wherein the first positioning portions are grooves, the engaging portions are protrusions.

17. The electronic device as claimed in claim 15, wherein the second positioning portions respectively comprise a ditch and a wall for engaging the engaging portions and for limiting the engaging portions against movement.

* * * * *